United States Patent
Eastham et al.

(10) Patent No.: US 10,464,875 B2
(45) Date of Patent: Nov. 5, 2019

(54) PROCESS FOR THE PRODUCTION OF ETHYLENICALLY UNSATURATED CARBOXYLIC ACIDS OR ESTERS

(71) Applicant: LUCITE INTERNATIONAL UK LIMITED, Billingham (GB)

(72) Inventors: Graham Ronald Eastham, Redcar (GB); David William Johnson, Redcar (GB); Mark Waugh, Redcar (GB); Jonathan Ainsley Iggo, Liverpool (GB); Michael Beaumont, Liverpool (GB)

(73) Assignee: LUCITE INTERNATIONAL UK LIMITED, Billingham (GB)

( * ) Notice: Subject to any disclaimer, the term of this patent is extended or adjusted under 35 U.S.C. 154(b) by 0 days.

(21) Appl. No.: 15/566,082

(22) PCT Filed: Apr. 12, 2016

(86) PCT No.: PCT/GB2016/051026
§ 371 (c)(1),
(2) Date: Oct. 12, 2017

(87) PCT Pub. No.: WO2016/166525
PCT Pub. Date: Oct. 20, 2016

(65) Prior Publication Data
US 2018/0093937 A1 Apr. 5, 2018

Related U.S. Application Data

(60) Provisional application No. 62/147,347, filed on Apr. 14, 2015.

(30) Foreign Application Priority Data

Apr. 14, 2015 (GB) .................. 1506308.4

(51) Int. Cl.
| | | |
|---|---|---|
| C07C 51/353 | (2006.01) | |
| C07C 67/343 | (2006.01) | |
| C07C 57/04 | (2006.01) | |
| C07C 69/54 | (2006.01) | |

(52) U.S. Cl.
CPC ............ *C07C 51/353* (2013.01); *C07C 57/04* (2013.01); *C07C 67/343* (2013.01); *C07C 69/54* (2013.01); *C07C 2523/02* (2013.01); *C07C 2527/167* (2013.01); *C07C 2527/232* (2013.01)

(58) Field of Classification Search
CPC ..... C07C 51/353; C07C 57/04; C07C 67/343; C07C 69/54

USPC ......................................................... 562/599
See application file for complete search history.

(56) References Cited

U.S. PATENT DOCUMENTS

| | | | |
|---|---|---|---|
| 2,313,501 A * | 3/1943 | Bryant et al. | |
| 6,509,493 B1 * | 1/2003 | Falkenberg et al. | |
| 6,544,924 B1 | 4/2003 | Jackson et al. | |
| 9,199,907 B2 * | 12/2015 | York | B01J 35/002 |

FOREIGN PATENT DOCUMENTS

| | | | |
|---|---|---|---|
| GB | 1 418 451 A | * | 12/1975 |
| GB | 1418451 A | | 12/1975 |
| JP | H0648977 A | | 2/1994 |
| RU | 2621687 C2 | | 3/2016 |
| WO | 9829379 A1 | | 7/1998 |
| WO | WO 98/29379 A1 | * | 9/1998 |
| WO | 958298 A2 | | 10/2000 |

OTHER PUBLICATIONS

Cong Lin et al: "Supporting Information. Direct ortho—Thiolation of Arenes and Alkenes by Nickel Catalysis",Organ Ic Letters,vol. 17, No. 5, Mar. 6, 2015 (Mar. 6, 2015), pp. S2-S98.*
Chao Feng et al: "Supporting Information. Rhodium(III)-catalyzed direct C—H allylation of electron-deficient alkenes with allyl acetates",Chemical Communications—CHEMCOM,vol. 51, No. 2, Jan. 7, 2015 (Jan. 7, 2015), pp. S1-S43.*
Chemical Abstracts Service; Shingo et al: "Preparation of methacrylic acid and derivatives thereof",retrieved from STN Database accession No. 1994:509856 ; -& JP H06 48977 A (Daicel Chem) Feb. 22, 1994.*
International Search Report for PCT/GB2016/051026 dated Jun. 21, 2016 (6 pages).
Cong Lin et al, "Direct ortho—Thiolation of Arenes and Alkenes by Nickel Catalysis", Organic Letters, vol. 17, No. 5, 6, Mar. 6, 2016, pp. 1328-1331 with supporting information (102 pages total).
Chao Feng et al, "Rhodium (III)-Catalyzed Direct C—H allylation of Electron-Deficient Alkenes with Allyl Acetates" Chemical Communications—CHEMCOM, vol. 51, No. 2, pp. 342-345 Jan. 7, 2015, with supporting information (47 pages total).
Oda Shingo et al, "Preparation of Methacrylic Acid And Derivatives Thereof", Database accession No. 1994:509856.
Patrizia Lorusso, et al, "α.-Methylenation of Methyl Propanoate by the Catalytic Dehydrogenation of Methanol", ChemCatChem, vol. 8, No. 1, pp. 222-227 (6 pages) Jan. 7, 2016.

* cited by examiner

*Primary Examiner* — Deborah D Carr
(74) *Attorney, Agent, or Firm* — Shumaker, Loop & Kendrick, LLP

(57) ABSTRACT

The present invention relates to a process for the production of an ethylenically unsaturated carboxylic acid or ester, preferably α,β ethylenically unsaturated carboxylic acids or esters, by the liquid phase reaction of formaldehyde or a suitable source thereof with a non-cyclic carboxylic acid ester in the presence of a basic metal salt.

16 Claims, No Drawings

PROCESS FOR THE PRODUCTION OF ETHYLENICALLY UNSATURATED CARBOXYLIC ACIDS OR ESTERS

BACKGROUND

The present invention relates to a process for the production of ethylenically unsaturated carboxylic acids or esters, particularly α, ß unsaturated carboxylic acids or esters, more particularly acrylic acids or esters such as (alk)acrylic acids or alkyl (alk)acrylates particularly (meth)acrylic acid or alkyl (meth)acrylates such as methyl (meth)acrylates by the condensation of carboxylic acid esters with formaldehyde or a source thereof in the presence of bases, in particular, but not exclusively, a process for the production of (meth)acrylic acid or alkyl esters thereof, for example, methyl methacrylate, by the condensation of propionic alkyl esters, for example methyl propionate, with formaldehyde or a source thereof in the presence of such a base. The invention is particularly relevant to the production of methacrylic acid (MAA) and methyl methacrylate (MMA).

Such acids or esters may be made by reacting an alkanoic ester of the formula $R^3$—$CH_2$—$COOR^4$, where $R^3$ and $R^4$ are each, independently, a suitable substituent known in the art of acrylic compounds such as an alkyl group, especially a lower alkyl group containing, for example, 1-4 carbon atoms, with a suitable methylene source such as formaldehyde. Thus, for instance, methacrylic acid or alkyl esters thereof, especially methyl methacrylate, may be made by the catalytic reaction of methyl propionate, with formaldehyde as a methylene source.

U.S. Pat. No. 485,070 describes the production of α,ß unsaturated aliphatic carboxylic acids by the vapour phase condensation of a saturated aliphatic monocarboxylic acid with formaldehyde using a caesium catalyst supported on a porous silica gel. The production of methacrylic acid from propionic acid and formaldehyde in the presence of the caesium/silica catalysts is carried out at temperatures ranging from 273° C. to 408° C. with the selectivity for methacrylic acid ranging from 81 to 88%.

As mentioned above, a known production method for MMA is the catalytic conversion of methyl propionate (MEP) to MMA using formaldehyde. U.S. Pat. No. 6,544,924 describes the production of ethylenically unsaturated acids or esters by the catalytic reaction of an alkanoic acid or ester, especially methyl propionate, with formaldehyde in the presence of a silica supported catalyst. The production of methyl methacrylate (MMA) and methacrylic acid (MA) from methyl propionate, methanol and formalin using these catalysts was carried out at 350° C. and resulted in yields of MMA and MA between 3 and 12% and selectivities for MMA and MA between 88 and 97%.

The problem with heterogenous systems is that high temperatures are required which increases expense and also increase the production of unwanted by-products.

WO00/58298 discloses that drying agents can be used in the reaction of lactones with a source of formaldehyde in the presence of a base to remove water, the sources of formaldehyde are polyoxymethylene or aldehydes. The lactone intermediates are very stable to hydrolysis and are highly activated due to the ring structure and both heterogenous and homogenous base catalysts are discussed. On the other hand, a linear ester is much more susceptible to hydrolysis and is much less activated.

SUMMARY

Surprisingly, it has now been found that particular metal salts are remarkably effective at improving the both yield and selectivity in the liquid phase reaction of the carboxylic acid ester with formaldehyde or a source thereof.

DETAILED DESCRIPTION

According to a first aspect of the present invention there is provided a process for the production of an ethylenically unsaturated carboxylic acid or ester, preferably, an α,ß ethylenically unsaturated carboxylic acid or ester, by the liquid phase reaction of formaldehyde or a suitable source thereof with a non-cyclic carboxylic acid ester in the presence of a basic metal salt.

Base

Preferably, the basic metal salt is a group I or a group II metal salt. Preferably, the basic metal salt is selected from group I or group II metal oxides, hydroxides, carbonates, hydrogen carbonates, methyl carbonates, alkoxides, such as methoxides and t-butoxides, fluorides and phosphates, more preferably, the basic metal salt is selected from group I or group II metal methoxides, carbonates or methyl carbonates. For the avoidance of doubt, by group I metals as used herein is meant lithium (Li), sodium (Na), potassium (K), rubidium (Rb), and caesium (Cs). For the avoidance of doubt, by group II metals as used herein is meant beryllium (Be), magnesium (Mg), calcium (Ca), strontium (Sr), barium (Ba). Preferably, the group I or group II metal is selected from potassium (K), caesium (Cs), rubidium (Rb) or barium (Ba), more preferably, from caesium (Cs) or rubidium (Rb).

Preferably, the basic metal salt may be selected from potassium oxide, caesium oxide, sodium oxide, rubidium oxide, barium oxide, potassium hydroxide, caesium hydroxide, sodium hydroxide, rubidium hydroxide, barium hydroxide, potassium phosphate, caesium phosphate, sodium phosphate, rubidium phosphate, barium phosphate, sodium methoxide, potassium methoxide, rubidium methoxide, sodium t-butoxide, potassium t-butoxide, rubidium t-butoxide, caesium t-butoxide, sodium fluoride, potassium fluoride, rubidium fluoride, caesium fluoride, potassium carbonate, caesium carbonate, sodium carbonate, rubidium carbonate, barium carbonate, potassium hydrogen carbonate, sodium hydrogen carbonate, rubidium hydrogen carbonate, caesium hydrogen carbonate, barium hydrogen carbonate, potassium methyl carbonate, sodium methyl carbonate, caesium methyl carbonate, rubidium methyl carbonate or barium methyl carbonate, more preferably, caesium methoxide, rubidium methoxide, caesium carbonate, rubidium carbonate, caesium methyl carbonate or rubidium methyl carbonate, most preferably, caesium carbonate or caesium methyl carbonate, especially, caesium methyl carbonate.

Suitable basic metal salts include carbonates (including the hydrogen and methyl carbonates) of caesium (Cs) or rubidium (Rb). Advantageously, the basic metal salts of the present invention give remarkably high conversions and selectivities for the reaction products of the invention.

Suitable basic group I or II metal salts are those group I or II metal salts which are at least partially soluble in the reaction medium at temperatures up to 300° C., more typically, at temperatures up to 250° C., most preferably, at temperatures up to 200° C.

The basic metal salt may be present in the reaction medium during the reaction in any suitable form. Preferably, the basic metal salt may be substantially fully dissolved in the reaction medium or the reaction medium and the basic metal salt together may be in the form of a slurry, wherein a proportion of the basic metal salt is dissolved in the reaction medium/liquid phase and a proportion is undissolved and therefore remains in the solid form. More preferably, the basic metal salt is substantially fully dissolved in the reaction medium/liquid phase.

A continuous reaction may be run with some of the reactants in the solid phase, but is preferably run with the reactants substantially fully solubilised.

A batch reaction may be run with some of the reactants in the solid phase, but is preferably run with the reactants substantially fully solubilised. Without being bound by theory, in a batch reaction the reaction medium and the basic metal salt together may be in the form of a slurry at the beginning of the process but more of the basic metal salt may become dissolved in the reaction medium as the process progresses due to the formation of methanol, in which the basic metal salt may be more soluble, such that the basic metal salt may be substantially fully dissolved at the end of the process. It will be appreciated by a person skilled in the art that reference to the amount of basic metal salt dissolved in the reaction medium is the amount dissolved in the reaction medium when it is at the temperature at which the reaction will be performed.

Preferably, the basic metal salt is fully saturated in the reaction medium. Preferably, when the basic metal salt is fully saturated in the reaction medium, any basic metal salt that is present in the undissolved form may be able to dissolve in the reaction medium as the dissolved base is reacted.

Preferably, at least part of the basic metal salt is in the liquid phase during the reaction.

The said basic metal salts of the present invention may provide from 90 to 100 wt % of the total metal present in the reaction medium, such as from 95, 99, 99.5 or 99.9 wt % of the total metal present in the reaction medium, more preferably substantially 100 wt % of the total metal present in the reaction medium based on the total solid weight of metals present in the reaction medium. Typically, no other metal types are present in the reaction medium of the present invention above a trace level other than the basic metal salts as defined herein, in particular no other metal types than group I metal salts are present in the reaction medium, more particularly, no other metal types than the group I metal salts as defined more particularly herein.

Thus, according to a second aspect of the present invention there is provided a process for the production of an ethylenically unsaturated carboxylic acid or ester, preferably, an α,β ethylenically unsaturated carboxylic acid or ester, by the liquid phase reaction of formaldehyde or a suitable source thereof with a non-cyclic carboxylic acid ester in the presence of a homogeneous basic metal salt.

Formaldehyde

A suitable source of formaldehyde may be a compound of formula I

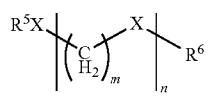

I wherein $R^5$ and $R^6$ are independently selected from $C_1$-$C_{12}$ hydrocarbons or H, X is O, n is an integer from 1 to 100, and m is 1.

Preferably, $R^5$ and $R^6$ are independently selected from $C_1$-$C_{12}$ alkyl, alkenyl or aryl as defined herein, or H, more preferably, $C_1$-$C_{10}$ alkyl, or H, most preferably, $C_1$-$C_6$ alkyl or H, especially, methyl or H. Preferably, n is an integer from 1 to 10, more preferably 1 to 5, especially, 1-3. However, other sources of formaldehyde may be used including trioxane.

Therefore, a suitable source of formaldehyde includes any equilibrium composition which may provide a source of formaldehyde. Examples of such include but are not restricted to methylal (1,1 dimethoxymethane), trioxane, polyoxymethylenes $R^1$—O—$(CH_2$—O$)_i$—$R^2$ wherein $R^1$ and/or $R^2$ are alkyl groups or hydrogen, i=1 to 100, paraformaldehyde, formalin (formaldehyde, methanol, water) and other equilibrium compositions such as a mixture of formaldehyde, methanol and methyl propionate. However, sources of formaldehyde containing more than 30% water are not used in the reaction or are at least preferably not used in the reaction.

Typically, the polyoxymethylenes are higher formals or hemiformals of formaldehyde and methanol $CH_3$—O—$(CH_2$—O$)_i$—$CH_3$ ("formal-i") or $CH_3$—O—$(CH_2$—O$)_i$—H ("hemiformal-i"), wherein i=1 to 100, preferably, 1-5, especially 1-3, or other polyoxymethylenes with at least one non methyl terminal group. Therefore, the source of formaldehyde may also be a polyoxymethylene of formula $R^{31}$—O—$(CH2$-O—$)_i R^{32}$, where $R^{31}$ and $R^{32}$ may be the same or different groups and at least one is selected from a $C_2$-$C_{10}$ alkyl group, for instance $R^{31}$=isobutyl and $R^{32}$=methyl.

Formalin may be used as a feedstock for formaldehyde but is generally de-watered prior to use in the reaction. Preferably, by the term formalin is meant a mixture of formaldehyde:methanol:water in the ratio 25 to 65%:0.01 to 25%:25 to 70% by weight. More preferably, by the term formalin is meant a mixture of formaldehyde:methanol:water in the ratio 30 to 60%:0.03 to 20%:35 to 60% by weight. Most preferably, by the term formalin is meant a mixture of formaldehyde:methanol:water in the ratio 35 to 55%:0.05 to 18%:42 to 53% by weight.

Preferably, a suitable source of formaldehyde may be selected from formalin (formaldehyde, methanol, water), low molecular weight polyformaldehyde (paraformaldehyde), gaseous formaldehyde, formaldehyde hemiacetal (alcoform), trioxane or anhydrous formaldehyde, more preferably, low molecular weight polyformaldehyde (paraformaldehyde), formaldehyde hemiacetal (alcoform) or anhydrous formaldehyde, most preferably, formaldehyde hemiacetal (alcoform) or anhydrous formaldehyde, especially, a suitable source of formaldehyde may be formaldehyde hemiacetal (alcoform). The use of paraformaldehyde, trioxane, anhydrous formaldehyde and formaldehyde hemiacetal (alcoform), especially, formaldehyde hemiacetal (alcoform) is preferred since this reduces the need to remove water from the process.

Preferably, the reaction mixture, for example the mixture comprising formaldehyde or a suitable source thereof and a non-cyclic carboxylic acid ester, contains less than about 5% water by weight (w/w). More preferably, the reaction mixture, for example the mixture comprising formaldehyde or a suitable source thereof and a non-cyclic carboxylic acid ester, contains less than about 2% water by weight. Most preferably, the reaction mixture, for example the mixture comprising formaldehyde or a suitable source thereof and a non-cyclic carboxylic acid ester, may contain from about 0.1 to 1.0% water by weight.

Preferably, the formaldehyde or suitable source thereof may have a water content of less than about 15% by weight (w/w), more preferably less than about 5% w/w, most preferably less than about 1% w/w. Preferably, the formaldehyde or suitable source thereof is essentially anhydrous.

In certain embodiments, the formaldehyde or suitable source thereof is formaldehyde hemiacetal (alcoform). Advantageously, the use of formaldehyde hemiacetal (alcoform) provides anhydrous formaldehyde.

Solvent

As detailed above, the formaldehyde or suitable source thereof and non-cyclic carboxylic acid ester and the basic metal salt are in the liquid phase. This liquid reaction medium may include a solvent for the reaction.

Accordingly, the process of the present invention may optionally further comprise one or more solvents.

Preferably, the solvent is wholly or substantially aprotic. Suitable aprotic solvents are tabulated in Table A-1, pp 112-114, of "Non-Aqueous Elelctrolyte Solutions in Chemistry and Modern Technology" by Josef Barthel, Heiner-J. Gores, Georg Schmeer and Rudolf Wachter, Topics in Current Chemistry, Vol. 111, page 33, 1983, under the headings "Aprotic protophilic solvents", "Aprotic protophobic solvents", "Low permittivity electron donor solvents" and "Inert solvents". Preferably, the solvent is an aprotic protophilic solvent or an aprotic photophobic solvent, more preferably, an aprotic protophilic solvent. Preferably the solvent is selected from dimethyl formamide, diethyl formamide, dimethylacetamide (DMAc), 1,3-dimethyl-3,4,5,6-tetrahydro-2(1H)-pyrimidinone (DMPU), 1,3-dimethyl-2-imidazolidinone (DMEU or DMI), 3-methyl-2-oxazolidinone, propylene carbonate, diethylacetamide, 1-methyl-2-pyrrolidinone, hexamethylphosphoric triamide, pyridine, tetramethyl urea, dimethylsulfoxide, acetonitrile, propionitrile, benzonitrile, acetone, 2-butanone, 3-pentanone, acetophenone, nitromethane, nitrobenzene, tetrahydrothiophene 1,1-dioxide (sulfolane), diethyl ether, diisopropyl ether, 1,4-dioxane, dimethyl carbonate, tetrahydrofuran, 1,2-dimethoxyethane, diglyme, benzene, cyclohexane, xylene or toluene. More preferably, the solvent is selected from dimethyl formamide, diethyl formamide, dimethylacetamide (DMAc), 1,3-dimethyl-3,4,5,6-tetrahydro-2(1H)-pyrimidinone (DMPU), 1,3-dimethyl-2-imidazolidinone (DMEU or DMI), 3-methyl-2-oxazolidinone, diethylacetamide, 1-methyl-2-pyrrolidinone, hexamethylphosphoric triamide, pyridine, tetramethyl urea, dimethylsulfoxide, acetonitrile, propionitrile, benzonitrile, acetone, 2-butanone, 3-pentanone, acetophenone, nitromethane, nitrobenzene, tetrahydrothiophene 1,1-dioxide (sulfolane), diethyl ether, diisopropyl ether, 1,4-dioxane, tetrahydrofuran, 1,2-dimethoxyethane or diglyme. Most preferably, the solvent is selected from dimethyl formamide, diethyl formamide, dimethylacetamide (DMAc), 1,3-dimethyl-3,4,5,6-tetrahydro-2(1H)-pyrimidinone (DMPU), 1,3-dimethyl-2-imidazolidinone (DMEU or DMI), 3-methyl-2-oxazolidinone, diethylacetamide, 1-methyl-2-pyrrolidinone, hexamethylphosphoric triamide, pyridine, tetramethyl urea, dimethylsulfoxide, acetonitrile, propionitrile, nitromethane or tetrahydrothiophene 1,1-dioxide (sulfolane).

It will be appreciated by a person skilled in the art that methanol or ethanol, when present, may be introduced to the reaction mixture from the source of formaldehyde. However, these alcohols should typically be used in conjunction with the solvents as detailed above and should be present in the reaction medium in amounts less than about 50 wt %, preferably, less than about 45 wt %, more preferably, less than about 20 wt % based on the total weight of the reaction medium.

Advantageously, the use of the solvents as described herein may improve the rate of the reaction.

Non-Cyclic Reactant

Preferably, the non-cyclic carboxylic acid ester reactant of the present invention is of the following formula:

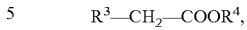

$$R^3-CH_2-COOR^4,$$

wherein $R^4$ is an alkyl group, preferably a $C_1$ to $C_4$-alkyl group, more preferably, a methyl group, and $R^3$ is a methyl group.

Thus, according to a further aspect of the present invention there is provided a process for the production of an ethylenically unsaturated carboxylic acid or ester, preferably, an α,β ethylenically unsaturated carboxylic acid or ester, by the liquid phase reaction of formaldehyde or a suitable source thereof with a non-cyclic carboxylic acid ester of formula $R^3-CH_2-COOR^4$ in the presence of a basic metal salt, wherein $R^4$ is an alkyl group, preferably a $C_1$ to $C_4$-alkyl group and $R^3$ is methyl.

Preferably, the non-cyclic carboxylic acid ester according to any aspect of the present invention is methyl propionate.

Products

Preferably, the ethylenically unsaturated carboxylic acid or ester, produced by the process of the present invention is selected from methacrylic acid, methyl methacrylate, ethyl methacrylate, propyl methacrylate or butyl methacrylate or the metal salt of methacrylic acid, most preferably, methyl methacrylate or the metal salt of methacrylic acid.

The process of the invention is particularly suitable for the production of methacrylic acid and its alkyl esters. Suitably, methacrylic acid and its esters are $(C_1-C_4)$alkyl methacrylates, typically produced from the reaction of the corresponding propionic acid ester with formaldehyde or a suitable source thereof in the presence of the basic metal salt, preferably, the production of methacrylic acid or especially methyl methacrylate (MMA) from methyl propionate.

In the present invention, the water produced in the condensation reaction may hydrolyse some of the ester formed in the process to the acid. Accordingly, this is one route to methacrylic acid.

Advantageously, the process of the present invention has been found to produce remarkably low levels of unwanted side products in the reaction of formaldehyde or a suitable source thereof with a non-cyclic carboxylic acid ester to produce an ethylenically unsaturated carboxylic acid or ester.

Advantageously, it has been shown that the selectivity for ethylenically unsaturated carboxylic acid or ester product of the process of the present invention does not substantially decrease with increased rates of conversion as would normally be expected. Typically, in processes of the prior art selectivity decreases as the rate of conversion increases due, without being bound by theory, to the production of more unwanted side products during the reaction at said higher rates of conversion. However, in the process of the present invention remarkably low levels of unwanted side products are produced and, therefore, the process of the present invention has surprisingly been found to produce improved rates of conversion whilst maintaining, or improving, selectivity for the ethylenically unsaturated carboxylic acid or ester product.

Furthermore, the major by-product of the present invention is the methanol adduct to the methacrylate ester (methyl 3-methoxyisobutyrate) or the base metal salt of the methanol adduct to methacrylic acid (metal 3-methoxyisobutyrate). These can be converted readily to the corresponding methacrylate by a base catalysed process (either in situ or in a separate process). Therefore, these by-products do not lead to irreversible selectivity loss and can necessarily be discounted when calculating the overall selectivity of the reaction.

According to a further aspect of the present invention there is provided an ethylenically unsaturated carboxylic acid or ester, preferably, an α,β ethylenically unsaturated carboxylic acid or ester, produced by the liquid phase reaction of formaldehyde or a suitable source thereof with a non-cyclic carboxylic acid ester in the presence of a basic metal salt.

According to a further aspect of the present invention there is provided methacrylic acid or methyl methacrylate produced by the liquid phase reaction of formaldehyde or a suitable source thereof with a non-cyclic carboxylic acid ester in the presence of a basic metal salt.

According to a further aspect of the present invention there is provided the use of a basic metal salt for the production of an ethylenically unsaturated carboxylic acid or ester, preferably, an α,β ethylenically unsaturated carboxylic acid or ester, by the liquid phase reaction of formaldehyde or a suitable source thereof with a non-cyclic carboxylic acid ester. Preferably, the invention provides use of the basic metal salt in the said reaction for improved selectivity, particularly methyl propionate (MeP) to methyl methacrylate (MMA) selectivity and/or formaldehyde to methyl methacrylate (MMA) selectivity, and/or for reduced temperature production and/or for reduced by-products, particularly higher boiling point by-products than the ethylenically unsaturated carboxylic acid or ester product.

Separation and/or purification of the ethylenically unsaturated carboxylic acid or ester, preferably α,β ethylenically unsaturated carboxylic acids or ester, from unreacted non-cyclic carboxylic acid or ester reactant may be performed by any suitable method known in the art.

Reaction Conditions

Preferably, the reaction may be performed at a temperature below about 300° C., more preferably, below about 280° C., most preferably, below about 240° C., especially, below about 190° C., for example, from about 80° C. to 250° C., more preferably from about 100° C. to 200° C., especially from about 120° C. to 190° C. Advantageously, the process of the present invention can be carried out at lower temperatures than would typically be expected from the prior art describing the gas phase reactions. This is particularly surprising given that the deprotonation of methyl propionate (MeP) in its reaction with formaldehyde occurs at high temperatures in industrial processes.

Preferably, the reaction may be performed at a pressure of between about 5 and 2000 psi, more preferably, between about 10 and 1000 psi, most preferably, between about atmospheric pressure or 14 and 500 psi. Typically, the reaction pressure may be selected such that the reactants are kept in the liquid phase at a given temperature.

The process of the present invention may be a batch or continuous process. Preferably, a continuous process is used.

The reagents may be fed to the reactor independently or after prior mixing.

The formaldehyde or suitable source thereof may be added to the reactor containing a reaction medium comprising the non-cyclic carboxylic acid ester together with the dissolved basic metal salt at any suitable rate. Typically, in a batch process the formaldehyde or suitable source thereof is added to the reactor containing a reaction medium comprising the non-cyclic carboxylic acid ester together with the dissolved basic metal salt at a rate which is suitable to maintain the non-cyclic carboxylic acid ester in a molar excess compared to the said formaldehyde or suitable source thereof.

By "molar excess" as used herein is meant, unless otherwise specified, that the formaldehyde or suitable source thereof is present in amounts at least 1 mol % lower, preferably, at least 5 mol % lower, more preferably, at least 10 mol % lower than the amount of non-cyclic carboxylic acid ester based on the total amount of formaldehyde or suitable source thereof and non-cyclic carboxylic acid ester present in the reaction medium.

For example, in a batch process the formaldehyde or suitable source thereof may be added to the reactor at a rate from about 1 to 10 mol %/minute relative to the non-cyclic carboxylic acid ester.

Preferably, the molar ratio of formaldehyde or suitable source thereof to the non-cyclic carboxylic acid ester is maintained at about 1:100 to 1:2, more preferably, about 1:50 to 1:5 throughout the duration of the process.

Preferably, in a batch reaction the molar ratio of basic metal salt to the non-cyclic carboxylic acid ester added to the reaction medium is about 5:1 to 0.2:1, more preferably, the molar ratio is about 2:1 to 0.4:1, most preferably, the molar ratio is about 2:1 to 0.5:1.

Preferably, the reaction medium composed of the non-cyclic carboxylic acid ester, basic metal salt and optional solvent is heated to around the temperature at which the reaction will be performed prior to addition of the formaldehyde or suitable source thereof. Preferably, the formaldehyde or suitable source thereof is heated to around the temperature at which the reaction will be performed prior to mixing with the reaction medium. It will be appreciated by a person skilled in the art that the reaction medium composed of the non-cyclic carboxylic acid ester, basic metal salt and optional solvent may be heated to a temperature 30° C. above or below the temperature at which the reaction will be performed.

Typically, during a continuous process the formaldehyde or suitable source thereof is added to the reactor, containing a reaction medium comprising the non-cyclic carboxylic acid ester together with the dissolved basic metal salt, at a rate which maintains the non-cyclic carboxylic acid ester in a molar excess compared to the said formaldehyde or suitable source thereof in the reaction medium. It will be appreciated by a person skilled in the art that in a continuous reaction the formaldehyde or suitable source thereof may be fed to the reaction medium comprising the non-cyclic carboxylic acid ester and the dissolved basic metal salt together with further non-cyclic carboxylic acid ester reactant and/or the basic metal salt.

For the avoidance of doubt, the term "molar excess" as used in reference to a continuous reaction has the same meaning as described above for a batch reaction.

Preferably, in a continuous reaction the formaldehyde or suitable source thereof may be fed to the reactor in a molar ratio of 1.1:1 to 1:1 with the non-cyclic carboxylic acid ester.

Preferably, in a continuous reaction the molar ratio of basic metal salt to the non-cyclic carboxylic acid ester may be maintained at 5:1 to 0.2:1, more preferably, about 2:1 to 0.4:1, most preferably, about 2:1 to 0.5:1 in the reaction medium.

Advantageously, in either a batch or a continuous reaction, adding the formaldehyde or suitable source thereof to the reactor in the manner as defined above, surprisingly, results in an improved rate of conversion. Advantageously, adding the formaldehyde or suitable source thereof to the reactor in the manner as defined above, surprisingly, limits the build up of formaldehyde thus reducing unwanted side reactions producing unwanted side products.

Advantageously, without being bound by theory, the addition of formaldehyde or suitable source thereof to the reaction medium containing the non-cyclic carboxylic acid ester together with the dissolved basic metal salt and optional solvent enables the formaldehyde to be heated to reaction temperature without any risk of decomposition catalysed by the basic metal salt.

In a batch reaction, contact times for the reactants in the presence of the basic metal salt are dependent on temperature, pressure and the concentration of the basic metal salt but are typically between 2 minutes and 12 hours, more preferably, 5 minutes and 8 hours, most preferably, 10 minutes and 4 hours.

In a continuous reaction average residence times in the reactor may correspond to the contact times in a batch reaction as set out above.

The amount of basic metal salt used in the process of the present invention is not necessarily critical and will be determined by the practicalities of the process in which it is employed. However, the amount of base will generally be chosen to effect the optimum selectivity and yield. Nevertheless, the skilled person will appreciate that the minimum amount of base should be sufficient to bring about sufficient deprotonation of the non-cyclic carboxylic acid ester to permit an acceptable rate of the reaction.

The relative amount of reagents used in or fed to the process of the invention can vary within wide limits but generally the mole ratio of formaldehyde or suitable source thereof to the non-cyclic carboxylic acid ester is within the range of 1:20 to 2:1, more preferably, 1:10 to 1.5:1, most preferably, 1:5 to 1.2:1. The most preferred ratio will depend on the form of the formaldehyde and the ability of the base to liberate formaldehyde from the formaldehydic species. Thus highly reactive formaldehydic substances where one or both of $R^{31}$ and $R^{32}$ in $R^{31}O\text{---}(CH_2\text{---}O\text{---})_iR^{32}$ is H require relatively low ratios, typically, in this case, the mole ratio of formaldehyde or suitable source thereof to the non-cyclic carboxylic acid ester is within the range of 1:9 to 1:1. Where the formaldehydic substances are of low reactivity, for instance where neither of $R^{31}$ and $R^{32}$ is H, as for instance in $CH_3O\text{---}CH_2\text{---}OCH_3$, or in trioxane higher ratios are most preferred, typically, 1:9 to 20:1.

The process according to any aspect of the present invention may optionally further comprise one or more alcohol(s). Preferably, an optional alcohol(s) for use in the basic reaction of the present invention is methanol. The amount of methanol is not critical. Generally, the amount used is as low as practicable allowing for its presence in some sources of formaldehyde, unless methanol is chosen as a reaction solvent as well, although, if desired, separate or further solvents may also be used.

The molar ratio of alcohol, when present in the reaction, to the non-cyclic acid ester is typically within the range 20:1 to 1:20, preferably 3:1 to 1:10, most preferably 2:1 to 1:5.

The molar ratio of methanol, when present in the reaction, to the non-cyclic acid ester is typically within the range 20:1 to 1:20, preferably 3:1 to 1:10, most preferably 2:1 to 1:5.

Drying Agents

As mentioned above, due to the source of formaldehyde, water may also be present in the reaction mixture. Depending on the source of formaldehyde, it may be necessary to remove some or all of the water therefrom prior to reaction. As mentioned above, maintaining lower levels of water than that in the source of formaldehyde may be advantageous to the reaction efficiency and/or subsequent purification of the products.

Therefore, the process of the present invention may optionally further comprise one or more drying agents. Suitable drying agents include anhydrous sodium sulphate, anhydrous magnesium sulphate, molecular sieves (various pore sizes), calcium oxide, calcium chloride, potassium carbonate, oxazolidines, orthoesters of the general formula $RC(OR')_3$, aluminum oxide, silica gel, activated carbon, montmorillonite and mixtures thereof.

Definitions

The term "alkyl" when used herein, means, unless otherwise specified, $C_1$ to $C_{12}$ alkyl and includes methyl, ethyl, ethenyl, propyl, propenyl butyl, butenyl, pentyl, pentenyl, hexyl, hexenyl and heptyl groups, preferably, methyl, ethyl, propyl, butyl, pentyl and hexyl. Unless otherwise specified, alkyl groups may, when there is a sufficient number of carbon atoms, be linear or branched, be cyclic, acyclic or part cyclic/acyclic, be unsubstituted, substituted or terminated by one or more substituents selected from halo, cyano, nitro, —$OR^{19}$, —$OC(O)R^{20}$, —$C(O)R^{21}$, —$C(O)OR^{22}$, —$NR^{23}R^{24}$, —$C(O)NR^{25}R^{26}$, —$SR^{29}$, —$C(O)SR^{30}$, —$C(S)NR^{27}R^{28}$, unsubstituted or substituted aryl, or unsubstituted or substituted Het, wherein $R^{19}$ to $R^{30}$ here and generally herein each independently represent hydrogen, halo, unsubstituted or substituted aryl or unsubstituted or substituted alkyl, or, in the case of $R^{21}$, halo, nitro, cyano and amino and/or be interrupted by one or more (preferably less than 4) oxygen, sulphur, silicon atoms, or by silano or dialkylsilcon groups, or mixtures thereof. Preferably, the alkyl groups are unsubstituted, preferably, linear and preferably, saturated.

The term "alkenyl" should be understood as "alkyl" above except at least one carbon carbon bond therein is unsaturated and accordingly the term relates to $C_2$ to $C_{12}$ alkenyl groups.

The term "alk" or the like should, in the absence of information to the contrary, be taken to be in accordance with the above definition of "alkyl".

The term "aryl" when used herein includes five-to-ten-membered, preferably five to eight membered, carbocyclic aromatic or pseudo aromatic groups, such as phenyl, cyclopentadienyl and indenyl anions and naphthyl, which groups may be unsubstituted or substituted with one or more substituents selected from unsubstituted or substituted aryl, alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$ or $C(S)NR^{27}R^{28}$ wherein $R^{19}$ to $R^{30}$ each independently represent hydrogen, unsubstituted or substituted aryl or alkyl (which alkyl group may itself be unsubstituted or substituted or terminated as defined herein), or, in the case of R, halo, nitro, cyano or amino.

The term "halo" when used herein means a chloro, bromo, iodo or fluoro group, preferably, chloro or fluoro.

The term "Het", when used herein, includes four- to twelve-membered, preferably four- to ten-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, alkyl (which alkyl group may itself be unsubstituted or substituted or terminated as defined herein) —OR$^{19}$, —OC(O)R$^{20}$, —C(O)R$^{21}$, —C(O)OR$^{22}$, —N(R$^{23}$)R$^{24}$, —C(O)N(R$^{25}$)R$^{26}$, —SR$^{29}$, —C(O)SR$^{30}$ or —C(S)N(R$^{27}$)R$^{28}$ wherein R$^{19}$ to R$^{30}$ each independently represent hydrogen, unsubstituted or substituted aryl or alkyl (which alkyl group itself may be unsubstituted or substituted or terminated as defined herein) or, in the case of R$^{21}$, halo, nitro, amino or cyano. The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

The terms "base" or "basic" when used herein, means, unless otherwise specified, a chemical species or molecular entity having at least one available pair of electrons capable of forming a covalent bond with hydrogen (proton) or with the vacant orbital of another species. The base may be a Brønsted base or a Lewis base. For the avoidance of doubt, a Brønsted base is a chemical species or molecular entity capable of accepting a hydrogen (proton) from an acid (i.e. a hydrogen acceptor) or the corresponding molecular entity or chemical species. For the avoidance of doubt, a Lewis base is a chemical species or molecular entity able to provide a pair of electrons and thus capable of coordination to a Lewis acid, thereby producing a Lewis adduct.

The term "reaction medium" as used herein means, unless otherwise specified, the liquid phase of the reaction.

The term "homogenous" as used herein means, unless otherwise specified, a process in which all the components, such as the reactants, the basic metal salt and, when present, the solvent are in the same phase.

The term "heterogenous" as used herein means, unless otherwise specified, a process in which one or more of the components, such as the reactants, the basic metal salt and, when present, the solvent are in a different phase from the remaining components.

The term "batch process" as used herein means, unless otherwise specified, a process in which a specified amount of reactants are reacted to obtain product under reaction conditions. The reaction generally continues until the reactants are used up.

The term "continuous process" as used herein means, unless otherwise specified, a process in which the reactants are fed into the reactor and products are taken out of the reactor after commencement of reaction and during the process. The reaction generally continues until the reactor is shut down.

Embodiments of the invention will now be described with reference to the following non-limiting examples and by way of illustration only.

EXAMPLES

All examples show the preparation of methyl methacrylate and methacrylic acid from methyl propionate.

Example 1

In a nitrogen-filled glovebox, a 25 mL Parr Series 4590 Pressure reactor autoclave was charged with 1.96 g caesium carbonate (6 mmol) and 6 mL N,N-dimethylacetamide. The autoclave was pressurized with nitrogen to 15 bar, purged slowly to 1.5 bar and then sealed. The mixture was then heated with stirring to 135° C. over 35 minutes. 2.65 g Methyl propionate (30 mmol) and 3 g methyl alcoform (55 mmol formaldehyde) were then injected under nitrogen pressure into the mixture in the autoclave. Injection caused a temperature decrease to 117° C. followed by a temperature spike to 155° C. After the temperature spike, the mixture was heated to 160° C. over 10 minutes. The mixture was maintained at the 160° C. for 4 hours after which stirring was stopped and the mixture cooled to below 25° C. The residual pressure was purged slowly and the exit mixture diluted with methanol until all of the salts had dissolved.

A sample of the solution was analysed by $^1$H NMR which showed the relative ratios were 68.0% methyl propionate: 15.7% caesium propionate:13.5% methyl methacrylate: 2.8% caesium methacrylate. The mixture was taken to dryness under high vacuum with collection of the volatile material in a liquid nitrogen trap. The reaction volatiles were analysed by GC and showed 15.8% conversion of methyl propionate to products and a selectivity with respect to methyl propionate to methyl methacrylate and methacrylic acid of 99.83%.

Example 2

In a nitrogen-filled glovebox, a 25 mL Parr Series 4590 Pressure reactor autoclave was charged with 2.5 g caesium methylcarbonate (12 mmol) and 6 mL N,N-dimethylacetamide. The autoclave was pressurized with nitrogen to 15 bar, purged slowly to 1.5 bar and then sealed. The mixture was heated with stirring to 135° C. over 35 minutes. 2.65 g methyl propionate (30 mmol) and 3 g methyl alcoform (55 mmol formaldehyde) were then injected under nitrogen pressure into the mixture in the autoclave. Injection caused a temperature decrease to 118° C. followed by a temperature spike to 152° C. After the temperature spike, the mixture was heated to 160° C. over 10 minutes. The mixture was maintained at the 160° C. for 4 hours after which stirring was stopped and the mixture cooled to below 25° C. The residual pressure was purged slowly and the exit mixture diluted with methanol until all of the salts had dissolved.

A sample of the solution was analysed by $^1$H NMR which showed the relative ratios were 69.8% methyl propionate: 9.4% caesium propionate:18.0% methyl methacrylate:2.8% caesium methacrylate. The mixture was taken to dryness under high vacuum with collection of the volatile material in a liquid nitrogen trap. The reaction volatiles were analysed by GC and showed 13.8% conversion of methyl propionate to products and a selectivity to methyl methacrylate and methacrylic acid of 99.25%.

Example 3

In a nitrogen-filled glovebox, a 25 mL Parr Series 4590 Pressure reactor autoclave was charged with 2.5 g caesium methylcarbonate (12 mmol) and 6 mL N,N-dimethylacetamide. The autoclave was pressurized with nitrogen to 15 bar, purged slowly to 1.5 bar and then sealed. The mixture was then heated with stirring to 135° C. over 35 minutes. 2.65 g methyl propionate (30 mmol) and 0.165 g methyl alcoform (3 mmol formaldehyde) were then injected under nitrogen pressure into the mixture in the autoclave. Injection caused a temperature decrease to 125° C. The mixture was then heated to 160° C. over 10 minutes and was maintained at this temperature for 2 hours after which stirring was stopped and the mixture cooled to below 25° C. The residual pressure was purged slowly and the exit mixture diluted with methanol until all of the salts had dissolved.

A sample of the solution was analysed by $^1$H NMR which showed the relative ratios were 78.0% methyl propionate: 16.0% caesium propionate:3.8% methyl methacrylate:2.2% caesium methacrylate. The mixture was taken to dryness under high vacuum with collection of the volatile material in a liquid nitrogen trap. The reaction volatiles were analysed by GC and showed 4.4% conversion of methyl propionate to products and a selectivity to methyl methacrylate and methacrylic acid of 99.64%.

Example 4

In a nitrogen-filled glovebox, a 25 mL Parr Series 4590 Pressure reactor autoclave was charged with 1.368 g potassium methylcarbonate (12 mmol) and 6 mL N,N-dimethylacetamide. The autoclave was pressurized with nitrogen to 15 bar, purged slowly to 1.5 bar and then sealed. The mixture was heated with stirring to 135° C. over 35 minutes. 2.65 g methyl propionate (30 mmol) and 0.33 g methyl alcoform (6.0 mmol formaldehyde) were then injected under nitrogen pressure into the mixture in the autoclave. Injection caused a temperature decrease to 118° C. followed by a temperature spike to 138° C. After the temperature spike, the mixture was heated to 160° C. over 10 minutes. The mixture was maintained at the 160° C. for 30 minutes after which stirring was stopped and the mixture cooled to below 25° C. The residual pressure was purged slowly and the exit mixture diluted with methanol until all of the salts had dissolved.

A sample of the solution was analysed by $^1$H NMR which showed the relative ratios were 84.3% methyl propionate: 10.3% potassium propionate:5.2% methyl methacrylate: 0.2% potassium methacrylate. The mixture was taken to dryness under high vacuum with collection of the volatile material in a liquid nitrogen trap. The reaction volatiles were analysed by GC and showed 5.5% conversion of methyl propionate to products and a selectivity to methyl methacrylate and methacrylic acid of 99.32%.

Example 5

In a nitrogen-filled glovebox, a 25 mL Parr Series 4590 Pressure reactor autoclave was charged with 2.5 g caesium methylcarbonate (12 mmol), 2.65 g methyl propionate (30 mmol) and 6 mL N,N-dimethylacetamide. The autoclave was pressurized with nitrogen to 15 bar, purged slowly to 1.5 bar and then sealed. The mixture was heated with stirring to 160° C. over 50 minutes. 1.65 g methyl alcoform (30 mmol formaldehyde) was then drip fed at 0.05 mL min$^{-1}$ for 33 minutes. The mixture was sealed and heated at 160° C. for a further 27 minutes after which stirring was stopped and the mixture cooled to below 25° C. The residual pressure was purged slowly and the exit mixture diluted with methanol until all of the salts had dissolved.

A sample of the solution was analysed by $^1$H NMR which showed the relative ratios were 55.2% methyl propionate: 24.2% caesium propionate:9.6% methyl methacrylate: 14.0% caesium methacrylate. The mixture was taken to dryness under high vacuum with collection of the volatile material in a liquid nitrogen trap. The reaction volatiles were analysed by GC and showed 23.9% conversion of methyl propionate to products and a selectivity to methyl methacrylate and methacrylic acid of 99.46%.

Example 6

In a nitrogen-filled glovebox, a 25 mL Parr Series 4590 Pressure reactor autoclave was charged with 2.5 g caesium methylcarbonate (12 mmol), 2.65 g methyl propionate (30 mmol) and 6 mL N,N-dimethylacetamide. The autoclave was pressurized with nitrogen to 15 bar, purged slowly to 1.5 bar and then sealed. The mixture was heated with stirring to 160° C. over 50 minutes. 1.65 g methyl alcoform (30 mmol formaldehyde) was then drip fed at 0.05 mL min$^{-1}$ for 33 minutes. The mixture was sealed and heated at 160° C. for a further 27 minutes after which stirring was stopped and the mixture cooled to below 25° C. The residual pressure was purged slowly and the exit mixture diluted with methanol until all of the salts had dissolved.

A sample of the solution was analysed by $^1$H NMR which showed the relative ratios of propionates and methacrylates were 56.3% methyl propionate:22.5% caesium propionate: 10.7% methyl methacrylate:10.5% caesium methacrylate. The mixture was taken to dryness under high vacuum with collection of the volatile material in a liquid nitrogen trap. The reaction volatiles were analysed by GC and showed 24.3% conversion of methyl propionate to products and a selectivity to methyl methacrylate and methacrylic acid of 99.13%.

Example 7

In a nitrogen-filled glovebox, a 25 mL Parr Series 4590 Pressure reactor autoclave was charged with 2.5 g caesium methylcarbonate (12 mmol), 2.65 g methyl propionate (30 mmol) and 6 mL N,N-dimethylacetamide. The autoclave was pressurized with nitrogen to 15 bar, purged slowly to 1.5 bar and then sealed. The mixture was heated with stirring to 160° C. over 50 minutes. 1.65 g methyl alcoform (30 mmol formaldehyde) was then drip fed at 0.05 mL min$^{-1}$ for 66 minutes. The mixture was sealed and the stirring was stopped and the mixture cooled to below 25° C. The residual pressure was purged slowly and the exit mixture diluted with methanol until all of the salts had dissolved.

A sample of the solution was analysed by $^1$H NMR which showed the relative ratios of propionates and methacrylates were 49.0% methyl propionate:27.0% caesium propionate: 12.0% methyl methacrylate:12.0% caesium methacrylate. The mixture was taken to dryness under high vacuum with collection of the volatile material in a liquid nitrogen trap. The reaction volatiles were analysed by GC and showed 25.5% conversion of methyl propionate to products and a selectivity to methyl methacrylate and methacrylic acid of 99.24%.

TABLE 1

Conversion and selectivity results for examples 1-7

| Example no. | 1 | 2 | 3 | 4 | 5 | 6 | 7 |
|---|---|---|---|---|---|---|---|
| Conversion/% | 15.8 | 13.8 | 4.4 | 5.5 | 23.9 | 24.3 | 25.5 |
| Selectivity/% | 99.83 | 99.25 | 99.64 | 99.32 | 99.46 | 99.13 | 99.24 |

Table 1 summarises the conversion and selectivity results for examples 1-7 and shows that selectivity is independent of yield for the reaction of the invention.

Examples 8-21

General Procedure

A 25 mL Parr Series 4590 Pressure reactor autoclave was charged with base metal salt (12 mmol), solvent (6 mL) and methyl propionate (2.65 g, 30 mmol), then pressurized with nitrogen to 15 bar, purged slowly to 1.5 bar and then sealed.

The mixture was heated with stirring to the reaction temperature over 50 minutes. Methyl alcoform (55 weight % formaldehyde, 45 weight % methanol) was added through dropwise addition at 0.05 mL min$^{-1}$ until the desired quantity had been added using a Gilson pump. The mixture was stirred for a time to complete the total reaction time at the reaction temperature after which stirring was stopped and the mixture cooled to room temperature. The residual pressure was purged slowly and the exit mixture diluted with methanol until all of the salts had dissolved.

MIB=methyl isobutyrate
DMAcr=dimethylacrylamide
MeP=methyl propionate
MMA=methyl methacrylate
HCHO=formaldehyde Excluding methyl 3-methoxyisobutyrate, which can be converted to MMA and methanol by mild treatment as shown in example 24, the selectivities are maintained at high selectivities over a range of conversions of methyl propionate to methyl propionate.

TABLE 2

Results from examples 8-21

| Example No. | 8 | 9 | 10 | 11 | 12 | 13 | 14 |
|---|---|---|---|---|---|---|---|
| Base Salt | CsMC | CsMC | CsMC | CsMC | CsMC | CsMC | CsMC |
| Solvent | DMAc | DMAc | DMAc | DMAc | DMAc | DMAc | DMAc |
| Feed Ratio HCHO:MeP | 0.5 | 1 | 1 | 1 | 1 | 1 | 1 |
| Moles Cs/Mole MeP | 0.4 | 0.4 | 0.4 | 0.4 | 0.4 | 0.4 | 0.4 |
| T | 160 | 160 | 160 | 160 | 160 | 160 | 180 |
| Feed Rate HCHO added/MeP equivalents/%/min | 6.45 | 6.45 | 6.45 | 6.45 | 6.45 | 6.45 | 6.45 |
| Total hold time incl feed time (hrs) | 1 | 1 | 0.5 | 2 | 3 | 4 | 1 |
| Conversion of Propionate to Methacrylate/% | 15.0 | 26.4 | 18.4 | 31.4 | 29.7 | 39.7 | 33.5 |
| Selectivity to methacrylates vs MeP excluding methyl 3-methoxy-isobutyrate/% | Not measured | 99.9 | 99.8 | 99.9 | 99.3 | 99.7 | |

| Example No. | 15 | 16 | 17 | 18 | 19 | 20 | 21 |
|---|---|---|---|---|---|---|---|
| Base Salt | KMC | CsMC | CsMC | CsMC | CsMC | CsMC | CsMC |
| Solvent | DMAc | NMP | DMAc | DMAc | DMAc | DMAc | DMAc |
| Feed Ratio HCHO:MeP | 1 | 1 | 1 | 1 | 1 | 1 | 1 |
| Moles Cs/Mole MeP | 0.4 | 0.4 | 0.4 | 0.4 | 0.4 | 0.4 | 0.4 |
| T° C. | 160 | 160 | 100 | 100 | 130 | 130 | 180 |
| Feed Rate HCHO added/MeP equivalents/%/min | 6.45 | 6.45 | 6.45 | 6.45 | 6.45 | 6.45 | 6.45 |
| Total hold time incl feed time (hrs) | 1 | 1 | 2 | 3 | 2 | 3 | 3 |
| Conversion of Propionate to Methacrylate/% | 12.7 | 26.6 | 1.5 | 2.1 | 12.8 | 14.5 | 39.5 |
| Selectivity to methacrylates vs MeP excluding methyl 3-methoxy-isobutyrate/% | 99.8 | 99.9 | 99.2 | 98.5 | 99.8 | 99.7 | 99.8 |

A sample of the solution was analysed by $^1$H NMR which showed the relative ratios of propionates and methacrylates as methyl propionate, propionate anion, methyl methacrylate and methacrylate anion. The mixture was taken to dryness under high vacuum with collection of the volatile material in a liquid nitrogen trap. The reaction volatiles were analysed by GC using an Agilent 6890N GC equipped with a Restek Rtx-1701 60 meter 0.32 mm ID, 1 micron df column.

Examples 8-21

Results

The data from the analyses carried out as described in the general procedure section above are shown in Table 2.
Abbreviations used in the table are as follows:
CsMC=caesium methylcarbonate
KMC=Potassium methylcarbonate
CsP=caesium propionate
CsMA=caesium methacrylate
DMAc=dimethylacetamide
NMP=1-methyl-2-pyrrolidinone Example 22

Into a 1 L Hastelloy autoclave was added Methyl propionate (160 ml), dry methyl alcoform (0.1 wt water) (140 ml, 55 wt % formaldehyde) and Caesium fluoride (145.5 g). The autoclave was then closed and then heated to 160° C. for two hours. The autoclave was allowed to cool to room temperature and the contents exited. The exit solution was heated under vacuum and the reaction volatiles condensed with liquid Nitrogen. The volatiles were allowed to thaw and were analysed by GC. The GC analysis showed 17.7% conversion of the MeP and a reaction selectivity of 99.7%.

Example 23

Into a 1 L Hastelloy autoclave was added Methyl propionate (160 ml), dry methyl alcoform (0.1 wt water) (140 ml, 55 wet % formaldehyde), methanol (100 ml) and Caesium fluoride (156.6 g). The autoclave was then closed and then heated to 160° C. for two hours. The autoclave was allowed to cool to room temperature and the contents exited. The exit solution was heated under vacuum and the reaction volatiles condensed with liquid Nitrogen. The volatiles were allowed to thaw and were analysed by GC. The GC analysis showed 8.0% conversion of the MeP and a reaction selectivity of 96.6%.

Example 24

Conversion of Methyl 3-Methoxyisobutyrate to MMA

Into a 100 ml Schlenk flask under Nitrogen was added Sodium methoxide (NaOMe; 0.61 g, 11 mmol), this was dissolved in methanol (16.16 g, 517 mmol). Into a separate 250 ml Schlenk flask under Nitrogen was added the methyl 3-methoxyisobutyrate (66.78 g, 505 mmol) and this was heated to 95° C. Once the temperature had stabilised, the NaOMe and methanol solution was added to the methyl 3-methoxyisobutuyrate using a cannula under Nitrogen. A sample of the resultant solution was taken every two minutes for ten minutes, and then 15 minutes for an hour. The samples were passed through silica gel to remove any NaOMe. The samples were then analysed by the use of a GC. After one hour the percentage conversion of methyl 3-methoxyisobutyrate to MMA was 37.27%.

Comparative Example 25

A silica gel catalyst with composition 0.93 wt Zr, 6.35 wt Cs, prepared according to example 3B of WO 03026795, was tested for catalytic performance under conditions described below.

The catalytic performance of the catalyst samples was determined in an atmospheric pressure microreactor charged with 3 g of catalyst beads (2-4 mm diameter). The dry catalysts heated to 350° C. under nitrogen and then fed with a mixture of 68.3 wt % methyl propionate, 19.5 wt % methanol, 6.8 wt % water and 5.4 wt % formaldehyde overnight at a residence time of about 16 seconds. The reaction was then switched to a feed mixture of 74.0 wt % methyl propionate, 19.9 wt % methanol, 0.5 wt % water and 5.6 wt % formaldehyde at such a rate that contact time was varied in steps from 2.9 seconds to 16.5 seconds. After the feed flow had stabilized at each flow rate, the gases from the reactor were condensed by cooling to room temperature and collected in glass vials via canulae fed through plastic lids of the vials to prevent ingress of air and condensation of water.

The samples were transferred to sealed vials immediately after completion of collection of each sample and were analysed by Gas Chromatography, using a Shimadzu GC, equipped with a DB1701 column & a Flame Ionization Detector, in order to determine composition. For each analysis, the resultant chromatograph was processed using Shimadzu's GC solution software to obtain peak areas for individual components. FID response factors for the individual components are applied to convert peak areas, first into wt, and then into mol, of detectable material in the sample.

The principle product was methyl methacrylate, which in addition to methacrylic acid, represents the desired product for calculation of reaction selectivity. Selectivity with respect to desired products was calculated from the sum of molar amount of the methyl methacrylate and methacrylic acid components produced as percentage of the molar amount of propionate converted to products. A part of the methyl propionate was converted to propionic acid. This by-product was excluded from the calculations on the basis that it can be readily converted back to the starting methyl propionate by esterification. All of the other products identified were irreversibly converted from the starting materials and are therefore not able to be recycled.

The identification of the major by-products was made by GCMS and the selectivities to these by-products based on methyl propionate converted to products other than propionic acid are shown in the table 3 below:

TABLE 3

| Results from comparative example 25 | | | | |
|---|---|---|---|---|
| Contact time/seconds | 2.90 | 4.72 | 7.59 | 16.46 |
| Main Product Yields/% | | | | |
| MeP Conversion to prods including Propionic Acid | 14.90 | 18.46 | 21.28 | 24.30 |
| Methylmethacrylate (MMA) | 11.30 | 14.14 | 16.03 | 17.10 |
| Methacrylic Acid (MAA) | 0.43 | 0.51 | 0.59 | 0.66 |
| MMA + MAA | 11.72 | 14.65 | 16.62 | 17.76 |
| Propionic Acid | 2.47 | 2.71 | 2.99 | 3.22 |
| MeP Reaction Selectivity-PA/% | | | | |
| MMA | 90.89 | 89.78 | 87.71 | 81.13 |
| MAA | 3.45 | 3.20 | 3.21 | 3.13 |
| MMA + MAA | 94.34 | 92.98 | 90.92 | 84.26 |
| Total Lights | 1.19 | 1.02 | 0.88 | 0.75 |
| Mediums | 0.25 | 0.31 | 0.43 | 0.88 |
| Heavy By-products | 4.22 | 5.69 | 7.77 | 14.11 |

Thus, the selectivity of conversion of methyl propionate of methyl methacrylate plus methacrylic acid falls from 94% to 84% as the yield is increased from 11.7% to 17.8% based on methyl propionate fed. None of the major by-products can be converted back to methyl methacrylate by simple chemical processing.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A process for production of an ethylenically unsaturated carboxylic acid or ester by a liquid phase reaction of formaldehyde or a suitable source thereof with a non-cyclic carboxylic acid ester of formula $R^3$—$CH_2$—$COOR^4$ in the presence of a basic metal salt, wherein $R^4$ is an alkyl group and $R^3$ is methyl wherein the basic metal salt is a group I or a group II metal salt.

2. The process according to claim 1, wherein the basic metal salt is selected from group I or group II metal oxides, hydroxides, carbonates, hydrogen carbonates, methyl carbonates, alkoxides, fluorides and phosphates.

3. The process according to claim 1, wherein the basic metal salt is selected from potassium oxide, caesium oxide, sodium oxide, rubidium oxide, barium oxide, potassium hydroxide, caesium hydroxide, sodium hydroxide, rubidium hydroxide, barium hydroxide, potassium phosphate, caesium phosphate, sodium phosphate, rubidium phosphate, barium phosphate, sodium methoxide, potassium methoxide, rubidium methoxide, sodium t-butoxide, potassium t-butoxide, rubidium t-butoxide, caesium t-butoxide, sodium fluoride, potassium fluoride, rubidium fluoride, caesium fluoride, potassium carbonate, caesium carbonate, sodium carbonate, rubidium carbonate, barium carbonate, potassium hydrogen carbonate, sodium hydrogen carbonate, rubidium hydrogen carbonate, caesium hydrogen carbonate, barium hydrogen carbonate, potassium methyl carbonate, sodium methyl carbonate, caesium methyl carbonate, rubidium methyl carbonate or barium methyl carbonate.

4. The process according to claim 1, wherein the reaction is performed at a temperature below 300° C.

5. The process according to claim 1, wherein the reaction is performed at a pressure of between 5 and 2000 psi.

6. The process according to claim 1, wherein the suitable source of formaldehyde is selected from formalin, low molecular weight polyformaldehyde, gaseous formaldehyde, formaldehyde hemiacetal, trioxane or anhydrous formaldehyde.

7. The process according to claim 1, wherein the process is a batch or continuous process.

8. The process according to claim 1, wherein in a reaction medium the non-cyclic carboxylic acid ester is maintained in a molar excess compared to the formaldehyde or suitable source thereof.

9. The process according to claim 8, wherein the formaldehyde or suitable source thereof is added to the reactor at a rate from about 1 to 10 mol %/minute relative to the non-cyclic carboxylic acid ester.

10. The process according to claim 8, wherein a molar ratio of formaldehyde or suitable source thereof to the non-cyclic carboxylic acid ester is maintained at about 1:100 to 1:2 during the reaction.

11. The process according to claim 8, wherein the formaldehyde or suitable source thereof is fed to a reactor in a molar ratio of 1.1:1 to 1:1 with the non-cyclic carboxylic acid ester.

12. The process of claim 1, further comprising one or more solvents.

13. The process according to claim 12, wherein the one or more solvents is wholly or substantially aprotic.

14. The process according to claim 13, wherein the solvent is an aprotic protophilic solvent or an aprotic photophobic solvent.

15. The process according to claim 14, wherein the solvent is selected from dimethyl formamide, diethyl formamide, dimethylacetamide (DMAc), 1,3-dimethyl-3,4,5,6-tetrahydro-2(1H)-pyrimidinone (DMPU), 1,3-dimethyl-2-imidazolidinone (DMEU or DMI), 3-methyl-2-oxazolidinone, propylene carbonate, diethylacetamide, 1-methyl-2-pyrrolidinone, hexamethylphosphoric triamide, pyridine, tetramethyl urea, dimethylsulfoxide, acetonitrile, propionitrile, benzonitrile, acetone, 2-butanone, 3-pentanone, acetophenone, nitromethane, nitrobenzene, tetrahydrothiophene 1,1-dioxide (sulfolane), diethyl ether, diisopropyl ether, 1,4-dioxane, dimethyl carbonate, tetrahydrofuran, 1,2-dimethoxyethane, diglyme, benzene, cyclohexane, xylene or toluene.

16. A process according to claim 1, wherein the ethylenically unsaturated carboxylic acid or ester is an α,β ethylenically unsaturated carboxylic acid or ester.

* * * * *